United States Patent [19]

Wright et al.

[11] Patent Number: 4,504,600

[45] Date of Patent: Mar. 12, 1985

[54] PROCESS FOR PRODUCING ALCOHOLS USING IRON-THALLIUM CATALYSTS

[75] Inventors: Franklin J. Wright, Watchung; Michael A. Richard, Fanwood; James C. Pirkle, Lebanon, all of N.J.

[73] Assignee: Exxon Research and Engineering Co., Florham Park, N.J.

[21] Appl. No.: 478,916

[22] Filed: Mar. 25, 1983

Related U.S. Application Data

[63] Continuation-in-part of Ser. No. 445,970, Dec. 1, 1982, abandoned, which is a continuation of Ser. No. 333,699, Dec. 23, 1981, abandoned.

[51] Int. Cl.$^3$ .......................... C07C 1/04; C07C 27/06
[52] U.S. Cl. .................... 518/717; 518/720; 518/721
[58] Field of Search ............... 518/714, 717, 719, 720, 518/721

[56] References Cited

U.S. PATENT DOCUMENTS

| 1,562,480 | 11/1925 | Wietzel et al. . |
| 2,711,420 | 6/1955 | Brown et al. . |
| 2,727,055 | 12/1955 | Seelig et al. . |
| 2,768,961 | 10/1956 | Weck et al. . |
| 2,815,357 | 12/1957 | Seelig et al. . |

FOREIGN PATENT DOCUMENTS

| 635950 | 6/1927 | France . |
| 300294 | 11/1928 | United Kingdom . |
| 866161 | 4/1961 | United Kingdom . |

OTHER PUBLICATIONS

U.S. Bureau of Mines Report No. 5456, (1959).

*Primary Examiner*—Howard T. Mars
*Attorney, Agent, or Firm*—Robert J. North; Edward H. Mazer

[57] ABSTRACT

CO hydrogenation process for producing alcohols is described utilizing novel thallium-promoted iron catalysts. Mixtures of $CO/H_2$ are selectively converted to liquid $C_6$–$C_{12}$ hydrocarbons containing $C_6$–$C_{12}$ alcohols with attendant low methane and low $CO_2$ make.

17 Claims, No Drawings

PROCESS FOR PRODUCING ALCOHOLS USING IRON-THALLIUM CATALYSTS

CROSS REFERENCE TO RELATED APPLICATIONS

This application is a continuation-in-part application of Ser. No. 445,970, filed Dec. 1, 1982, abandoned, being a Rule 60 Continuation of Ser. No. 333,699, filed Dec. 23, 1981 and abandoned on Dec. 1, 1982.

BACKGROUND OF THE INVENTION

The Fischer-Tropsch process is one of several processes involving the hydrogenation of carbon monoxide and is well-known for producing hydrocarbons, hydrocarbon fuels and oxygenates by contacting mixtures of carbon-monoxide/hydrogen with generally an iron-based catalyst. The produced oxygenates usually contain liquid linear primary alcohols, in which $C_1$–$C_4$ alcohols generally predominate.

An extensive amount of work has been carried out in an effort to modify and improve the selectivity of the process in producing $C_6$–$C_{12}$ alcohols, particularly under conditions of low methane and $CO_2$ make. Such a process is desired in the art since $C_6$–$C_{12}$ linear alcohols are industrially important and used in detergents and plasticizers.

SUMMARY OF THE INVENTION

It has been found that a composition comprising a mixture of iron compounds and thallium compounds is an effective catalyst in a CO hydrogenation process for selectively promoting the production of $C_6$–$C_{12}$ liquid alcohols with desirably attendant low methane and $CO_2$ production.

The catalyst composition contains compounds of iron and thallium in an iron-thallium weight ratio of 100:1 to 1:100, respectively, taken as the free metals, and the composition can be supported or unsupported and contain catalyst promoter agents and additives as well. In a preferred embodiment, the iron value in the composition is substantially in the trivalent state prior to pretreatment. After pretreatment, the active catalyst consists of iron in at least two states, one portion of the iron being in an oxidized state, the other portion being in a reduced or carbided state. Further, the process of producing higher alcohols, and particularly $C_6$–$C_{12}$ liquid alcohols, must be carried out at conditions of temperature, pressure, and gas composition which maintain the active catalyst in the two states, i.e., partially reduced.

Generally, the $C_6$–$C_{12}$ liquid alcohols produced in the process comprise at least about 5 weight percent, and preferably about 10 weight percent or greater of total hydrocarbons produced. Use of the catalyst composition allows the process to be conducted at relatively low temperatures, from about 150° to 230° C. and at low pressures, from about 1 to 75 atmospheres (0.1 to 7.5 MPa) after pretreatment at 270° C., 1 atm, 1:1 $H_2$/CO for 16 hr, at a space velocity of 500 volumes of gas per volume of catalyst per hour.

In accordance with this invention, there is provided a process for producing $C_6$–$C_{12}$ liquid hydrocarbons containing $C_6$–$C_{12}$ alcohols, comprising the steps of:

(a) first contacting a supported or unsupported catalyst composition comprising a mixture of iron compounds and thallium compounds, wherein the weight ratio of iron:thallium, taken as the free metals, is from about 100:1 to 1:100, with a CO/$H_2$ mixture in a 1:4 to 4:1 volume ratio, respectively, at 250° to 400° C., 0.1 to 10 MPa pressure and 10 to 10,000 v/v/hr., or equivalent conditions, to result in a partial reduction of said iron compounds; and (b) continuing said contacting described in step (a) at a temperature of about 150° to 230° C. to produce $C_6$–$C_{12}$ liquid hydrocarbons containing $C_6$–$C_{12}$ alcohols.

DESCRIPTION OF THE INVENTION AND PREFERRED EMBODIMENTS

The subject process is conducted by contacting a mixture of CO and $H_2$ with a supported or unsupported catalyst composition comprising a mixture of iron compounds and thallium compounds wherein the ratio of iron-thallium, taken as the free metals, is from about 100:1 to 1:100. A thorough description of operable iron-thallium catalysts useful in the process is given in related application, U.S. Ser. No. 418,380, hereby incorporated by reference, which describes catalyst components and weight ratios, additives, promoter agents, supports and the like, and methods of preparation.

By the term "mixtures of CO and $H_2$", as used herein, is meant mixtures of pure CO and $H_2$, or impure mixtures, also containing water, $CO_2$ and the like, and including "water gas", "synthesis gas", "Town gas" and the like. A preferred mixture is that produced by gasification apparatus, such as a Shell-Koppers Gasifier.

The ratio of CO and $H_2$ as CO/$H_2$, in the process is about 4:1 to 1:4, preferably 2:1 to 1:2, and particularly preferred about 1:1, respectively.

The temperature of the process is conducted in the range of about 150° to 230° C., preferably about 175° to 220° C., and particularly preferred of about 175° to 200° C.

The pressure of the CO/$H_2$ feedstream in the process is about 0.1 MPa to about 10 MPa (1 to 100 atmospheres) and preferably about 0.5 to 2.0 MPa and particularly preferred, about 0.8 to 1.6 MPa.

The space velocity of the CO/$H_2$ feedstream is maintained in the range of about 10 to 10,000 v/v/hr., preferably about 100 to 2500 v/v/hr. and particularly preferred of about 150 to 1200 v/v/hr.

A particularly preferred embodiment of the subject process comprises contacting a mixture of CO and $H_2$, in about a 1:1 volume ratio, respectively, with a catalyst composition comprising a mixture of iron oxide and thallium nitrate or oxide, the weight ratio of iron-thallium, taken as the free metals, in the composition, preferably being from about 100:1 to 35:65 and particularly preferred of about 100:10 to 80:20. The iron oxide of the catalyst composition contains iron value, substantially in the trivalent state, and thallium compound, preferably, is substantially impregnated on the surface of the iron catalyst composition. The catalyst is preferably supported on aluminum oxide, magnesium oxide, or mixtures thereof. Other supports include $SiO_2$, alkali-doped $Al_2O_3$, titania, zirconia, silicon carbide, $MgCO_3$ and mixtures thereof. It is necessary that the catalyst be pretreated in a manner which only partially, and not completely, reduces the predominantly trivalent iron to a mixture of trivalent and/or divalent iron and reduced and/or carbided iron. The pretreatment may be carried out at temperatures from 250° to 400° C. in a CO containing reducing atmosphere, preferably CO/$H_2$, at pressures in the range of 0.1 to 10 MPa for periods ranging from 1 to 50 hours to achieve partial and not complete reduction. A particularly preferred pretreatment is to treat the catalyst with a 1:1 $H_2/CO$ volume mixture at 270° C., 1 atm, 500 v/v/hr. for about 16 hours. Equivalent pretreatment conditions which also result in partial reduction of the iron compounds are also deemed to be included within the scope of this invention.

Following pretreatment, the process for producing maximum yields of $C_6-C_{12}$ alcohols must be conducted at conditions of temperature, pressure and gas composition which maintain the catalyst in the mixed iron valency state. In particular, the temperature should be below 230° C., and, preferably, below 220° C. when the process is carried out at ratios of CO and $H_2$ from 1:4 to 4:1, preferably 2:1 to 1:2, and particularly preferred about 1:1, respectively. The process is preferably conducted at a temperature of about 175° to 220° C., a pressure of about 0.5 to 2.0 MPa, and a space velocity of about 100 to 2500 v/v/hr. The resulting product liquid hydrocarbons in the $C_6-C_{12}$ range contain at least about 5 weight percent of $C_6-C_{12}$ alchols and less than about one weight percent $C_{21+}$ hydrocarbon waxes, in the preferred process, both based on the product weight of $C_6-C_{12}$ liquid hydrocarbons.

The apparatus which is used for the process can be any of the conventional types, wherein the catalyst is used in the form of a fixed bed, fluid bed, slurry and the like. Preferred is the catalyst in the form of a fixed or fluid bed.

The process is generally conducted by placing the process catalyst into the reaction zone of the reactor and pretreating the catalyst prior to the run. The pretreatment step must be conducted in a manner which converts the initially and predominantly trivalent iron into at least two states of oxidation. In a preferred embodiment, the iron in the initial catalyst mass is present in the trivalent state as $Fe^{3+}$, as in $Fe_2O_3$, and the thallium may be present in the trivalent state, as in $Tl_2O_3$, or in the monovalent state, as in $TlNO_3$ or $Tl_2O$. During pretreatment, trivalent and/or monovalent thallium is believed to be reduced to metallic thallium and trivalent iron is partially reduced to a mixture of trivalent, divalent and zerovalent iron and iron carbides. To achieve this state of the catalyst, the pretreatment is conducted by contacting the catalyst with a reducing gas such as $H_2$, CO or mixtures thereof, at an elevated temperature for a sufficient period of time to obtain a partially reduced iron catalyst exhibiting high alcohol selectivity during subsequent operation of the process. A preferred method of pretreatment is to pass a 1:1 mixture of $H_2/CO$ over the catalyst at 270° C., 0.1 MPa total pressure, and 500 v/v/hr. The Examples all utilize, for example, a 16-hour pretreatment.

Thermal analysis experiments have shown that the trivalent iron in $Fe_2O_3$ is reduced to a mixture of divalent and trivalent iron, as in $Fe_3O_4$ and reduced and carbided iron at these pretreatment conditions. Also, thermal analysis has shown that trivalent or monovalent thallium is reduced to metallic thallium at temperatures above about 240° C. and, therefore, the thallium is converted quantitatively to thallium metal during pretreatment at these preferred conditions. A theory that we do not wish to be bound by is that we believe that metallic thallium assists the subsequent reduction of trivalent iron in $Fe_2O_3$ to a mixture of trivalent and divalent iron as in $Fe_3O_4$ and reduced and carbided iron. With no metallic thallium present as promoter or with only a potassium promoter as, for example, potassium carbonate, the trivalent iron in $Fe_2O_3$ is not reduced to a mixture of $Fe_3O_4$, and reduced and carbided iron at the preferred pretratment conditions of 1:1 $H_2/CO$, 270° C., 0.1 MPa total pressure, 500 v/v/hr., for 16 hr. Thus, we believe that one of the actions provided by thallium as a promoter is to promote the reduction of trivalent iron.

After the pretreatment step, the temperature is reduced sufficiently to preclude further reduction of the iron in the catalyst and, thereby, to ensure that the iron value remains as a mixture of oxidized and reduced/carbided iron. We believe this active catalyst mixture to consist of metallic thallium, $Fe_3O_4$, metallic iron, and iron carbides such as $Fe_3C$ and $Fe_5C_2$. The feedstream gases, comprising CO and $H_2$, are then passed into the catalyst zone for reaction.

The hydrocarbons produced in the process comprise gaseous $C_1-C_4$ hydrocarbons and $C_5-C_{21}$ liquid hydrocarbons, a predominant fraction being $C_6-C_{12}$ liquid hydrocarbons, small amounts of $C_{21+}$ waxes, and linear $C_1-C_{19}$ alcohols, a predominant fraction being $C_6-C_{12}$ linear hydrocarbons, including methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, n-pentadecanol, n-hexadecanol, n-heptadecanol, n-octadecanol and n-nonadecanol.

"CO conversion" in the process is generally in the range of about 25 to 50%, as practiced on a laboratory scale, and can be substantially increased under the general reaction conditions described herein.

"$CO_2$ selectivity" in the process, as practiced, is generally below about 30%.

"Hydrocarbon selectivity" in the process, being the percent of converted CO leading to total hydrocarbons, including all gaseous, liquid, waxy hydrocarbons and oxygenates, is generally in the range of about 80 to 95% and can be decreased or increased under the general reaction conditions described herein.

Total $C_6-C_{12}$ hydrocarbons produced in the process are generally about 30 to 60 wt. % of total hydrocarbons produced.

Percent $C_1-C_{19}$ alcohols produced in the process is about 5 to 40 wt. % of the total hydrocarbons produced.

Total $C_6-C_{12}$ alcohols produced are at least 5 to about 4 wt. % of total $C_6-C_{12}$ hydrocarbons, and generally about 2 to 25 wt. % of total hydrocarbons produced. Preferably, the $C_6-C_{12}$ liquid hydrocarbons comprise about 10 weight percent and higher $C_6-C_{12}$ alcohols.

Percent methane produced in the process is generally about 1 wt. % of total hydrocarbons produced.

Percent $C_{21+}$ wax produced is in the range of about 2 to 4 wt. % based on total hydrocarbons produced. Some heavy carbonaceous materials may remain on the catalyst surface, after product collection, which aren't included in "total hydrocarbons", as reported in the specification examples.

Methods of collecting and separating the obtained alcohols in the process are conventional and include, for example, atmospheric and reduced pressure distillation.

The following examples illustrate the subject matter which we regard as our invention, and the examples are illustrative of the best mode of carrying out the invention, as contemplated by use, and should not be construed as being limitations on the scope and spirit of the instant invention.

EXAMPLE 1

Preparation of the Catalyst, 10:1 Fe/Tl

To a boiling solution of 404 g. ferric nitrate nonahydrate in 1.5 liters of distilled water was added with stirring a solution of 237 g. ammonium bicarbonate dissolved in 1.5 liters water resulting in the precipitation of iron oxide. The resulting solution was kept boiling until all $CO_2$ evolution had ceased. The precipitate was filtered, washed with distilled water until the wash water was neutral. The washed solid was dried in a vacuum at 110° C. for 12 hours. The resulting solid was impregnated by the technique of incipient wetness by the dropwise addition to the solid of a solution of 7.3 g. thallium nitrate in 70 ml. of water. The ferric oxide adsorbed practically all of the solution. The impregnated solid was dried in a vacuum oven at 110° C. for 12 hours. The resulting impregnated solid weighed 86 g. and analyzed for 10 parts by weight iron, per 1 part thallium, taken as the free metals.

The 10:1 Fe/Tl catalyst prepared as described above, was tested by the following procedure for Fischer-Tropsch synthesis of $C_6-C_{12}$ alcohols.

The catalyst was tested in a fixed bed tubular reactor fitted with a highly conductive brass sleeve. Catalyst pretreatment consisted of flowing a mixture of $H_2/CO/N_2$ (49:50:1, by volume, approx.) over the catalyst at 270° C., 1 atm. pressure, and a space velocity of 500 v/v/hr. for about 16 hours. At the end of this pretreatment, the runs were conducted at a temperature of either 175° C. or 200° C., a pressure of 120 psia or 240 psia and a space velocity of 150, 300 or 1200 v/v/hr. Liquid samples were collected at 4° C. and gas analyses were performed by in-line gas chromatography. A highly conductive brass sleeve was placed in the ¾-inch space between the surrounding furnace and the ½-inch O.D. stainless steel 3 cm. long reactor zone to (1) prevent natural convection of air which tends to lead to axial temperature gradients; and to (2) normalize and dissipate temperature gradients created by heats of reaction. The resulting data are shown below in Table I.

TABLE I

| Run | Temp. (°C.) | Sp. Vel. (v/v/hr.) | P (atm) | % CO Conv. | HC[a] Sel. | CH4[b] | % ROH[c] |
|---|---|---|---|---|---|---|---|
| 1 | 200 | 150 | 8.2 | 45 | 85 | 1.2 | 15 |
| 2 | 200 | 300 | 8.2 | 26 | 89 | 0.9 | 18 |
| 3 | 200 | 1200 | 8.2 | 10 | 98 | 1.4 | 25 |
| 4 | 175 | 150 | 8.2 | 28 | 98 | 0.3 | 28 |
| 5 | 200 | 150 | 16.3 | 40 | 88 | 1.0 | 21 |

[a]Percent total hydrocarbon selectivity.
[b]Methane produced - as weight percent of total hydrocarbons.
[c]Weight percent $C_6-C_{12}$ alcohols in $C_6-C_{12}$ hydrocarbons.

As is seen from the data, an increase in space velocity results in a corresponding increase in percent $C_6-C_{12}$ alcohol production and total hydrocarbon selectivity, a decrease in percent CO conversion, and relatively little change in methane production.

A decrease in temperature results in a corresponding decrease in percent CO conversion and methane production and an increase in $C_6-C_{12}$ alcohol production and total hydrocarbon selectivity.

An increase in the reaction pressure results in a decrease in the $C_6-C_{12}$ alcohol production and a significant increase in percent CO conversion.

EXAMPLE 2

A second run was made to determine the long-term stability of the iron/thallium catalyst during alcohol synthesis. Substantially the same catalyst was employed as in Example 1 with substantially the same pretreatment procedure prior to the run. The run was conducted at 200° C., $H_2/CO$ ratio of 1:1, 8.2 atmospheres and a space velocity of about 150 v/v/hr. The run was conducted continuously for 240 hours after pretreatment and on-line product analyses were conducted and liquid samples were collected and analyzed after 24, 72, 144, 192 and 240 hours on-stream. The results are listed below in Table II.

EXAMPLE 3

To show that the iron value in the working catalyst must be maintained in a state of multiple oxidation states, the catalyst from Example 2 was operated at conditions of temperature, pressure, space velocity and gas composition which caused the iron value in the working catalyst to be predominantly in the reduced or carbided state; these conditions being 270° C., 8.2 atm., 300 v/v/hr., and 1.1 $CO/H_2$. The results are shown in Table III. As seen under these conditions, the alcohol yield decreased with time. Simultaneously, the degree of reduction and carbide formation on the catalyst increased.

To show that this form of the catalyst is no longer as selective a catalyst for alcohol synthesis, the temperature was reduced to 175° to 200° C., with the other conditions being similar to Example 1, that is 8.2 to 16.3 atm., 300 v/v/hr. The activity of the catalyst was very low, as indicated by CO conversions in the range of 10 to 15%, the alcohol yields were also very low, as indicated by alcohol concentrations of less than 6% in the $C_6-C_{12}$ carbon number range. Because of the low activity, the yield of products was very low and more precise analyses of the products was not obtained. This example shows that the working catalyst for high alcohol yields should not be totally reduced or totally carbided, but rather it should consist of both partially oxidized and partially reduced iron. A theory that we do not wish to be bound by is that we believe that the partially oxidized regions of the catalyst provide the active centers for alcohol formation; whereas the reduced or carbided regions provide the active centers for more reduced hydrocarbons formation, as, for example, olefins, paraffins and aromatics.

TABLE II

| | Time (hours) | | | | |
|---|---|---|---|---|---|
| | 24 | 72 | 144 | 192 | 240 |
| % CO Conv. | 40–41 | 38–47 | 45–46 | 46 | 45 |
| $CO_2$ Sel.[a] | 15–18 | 13–15 | 13–17 | 11 | 12 |
| HC Sel.[b] | 85–82 | 87–85 | 87–83 | 89 | 88 |
| $C_1-C_{19}$ ROH[c] | 29.1 | 33.4 | 28.1 | 33.1 | 33.2 |
| $C_6-C_{12}$ ROH[d] | 4.7 | 8.1 | 7.6 | 7.6 | 7.5 |
| % $C_6-C_{12}$ ROH[e] | 15.9 | 18.0 | 17.6 | 17.9 | 18.8 |
| % Methane[f] | 1.1 | 0.1 | 0.9 | 0.8 | 0.9 |
| Wax collected[g] | 3.6 | 3.9 | 3.1 | 2.3 | 3.1 |

[a]Percent CO converted to $CO_2$.
[b]Percent CO converted to total hydrocarbons including alcohols.
[c]$C_1-C_{19}$ alcohols produced as wt. % of total produced hydrocarbons.
[d]$C_6-C_{12}$ alcohols as wt. % of total produced hydrocarbons.
[e]Weight percent $C_6-C_{12}$ alcohols of $C_6-C_{12}$ produced hydrocarbons.
[f]Percent methane produced as wt. % of total produced hydrocarbons.
[g]Percent $C_{20}+$ hydrocarbons as wt. % total hydrocarbons produced. Probably also present are some additional heavy hydrocarbons on the catalyst which did not breakthrough in 240 hours.

TABLE III

| | Time (hours) | | | |
|---|---|---|---|---|
| | 23 | 71 | 95 | 167 |
| % CO conv. | 65 | 64 | 65 | 68 |
| $CO_2$ Sel.[a] | 31 | 32 | 30 | 32 |
| HC Sel.[b] | 69 | 68 | 70 | 68 |
| $C_1$–$C_{19}$ ROH[c] | 17.9 | 8.4 | 8.1 | 7.0 |
| $C_6$–$C_{12}$ ROH[d] | 3.8 | 2.0 | 2.2 | 1.9 |
| % $C_6$–$C_{12}$ ROH[e] | 12.6 | 5.4 | 5.3 | 5.0 |
| % Methane | 4.3 | 4.7 | 4.5 | 4.8 |

[a] Percent CO converted to $CO_2$.
[b] Percent CO converted to total hydrocarbons including alcohols.
[c] $C_1$–$C_{19}$ alcohols produced as wt. % of total produced hydrocarbons.
[d] $C_6$–$C_{12}$ alcohols as wt. % of total produced hydrocarbons.
[e] Weight percent $C_6$–$C_{12}$ alcohols of $C_6$–$C_{12}$ produced hydrocarbons.
[f] Percent methane produced as wt. % of total produced hydrocarbons.
[g] Percent $C_{20}+$ hydrocarbons as wt. % total hydrocarbons produced. Probably also present are some additional heavy hydrocarbons on the catalyst which did not breakthrough in 240 hours.

What is claimed is:

1. A process for producing $C_6$–$C_{12}$ liquid hydrocarbons, containing $C_6$–$C_{12}$ alcohols, comprising the steps of:
   (a) first contacting a supported or unsupported catalyst composition comprising a mixture of iron compounds and thallium compounds, wherein the weight ratio of iron:thallium, taken as the free metals, is from about 100:1 to 1:100, with a $CO/H_2$ mixture in a 1:4 to 4:1 volume ratio, respectively, at 250 to 400° C., 0.1 to 10 MPa pressure and 10 to 10,000 v/v/hr, or equivalent conditions, to result in a partial, but not complete, reduction of said iron compounds to a mixture of trivalent and/or divalent iron and reduced and/or carbided iron; and
   (b) continuing said contacting described in step (a) at a temperature of about 150° to 230° C. to produce $C_6$–$C_{12}$ liquid hydrocarbons containing $C_6$–$C_{12}$ alcohols.

2. The process of claim 1 wherein said $C_6$–$C_{12}$ hydrocarbons comprise at least about 5 weight percent of $C_6$–$C_{12}$ alcohols.

3. The process of claim 2 wherein said $C_6$–$C_{12}$ hydrocarbons comprise about 10 weight percent $C_6$–$C_{12}$ alcohols.

4. The process of claim 1 wherein the weight ratio of iron-thallium, taken as the free metals, is from about 100:1 to about 35:65.

5. The process of claim 4 wherein said weight ratio of iron-thallium, taken as the free metals is from about 100:10 to 80:20.

6. The process of claim 1 wherein said catalyst is supported on $Al_2O_3$, alkali-doped $Al_2O_3$, $SiO_2$, $TiO_2$, MgO, $MgCO_3$, silicon carbide, zirconia, or mixtures thereof.

7. The process of claim 1 wherein said compounds of iron and thallium are selected from their oxides, hydroxides, carbonates, sulfates, carbides, halides, nitrates, or mixtures thereof.

8. The process of claim 7 wherein said iron compound is iron oxide.

9. The process of claim 7 wherein said thallium compound is thallium oxide, thallium chloride, thallium fluoride, thallium nitrate, or mixtures thereof.

10. The process of claim 1 wherein the mixture of CO and $H_2$ in steps (a) and (b) is in a volume ratio of about 2:1 to 1:2, respectively.

11. The process of claim 1 wherein said temperature in step (b) is about 175° to 220° C.

12. The process of claim 1 wherein said pressure in step (b) is about 0.5 to 2.0 MPa.

13. The process of claim 1 wherein said space velocity is in the range of about 100 to 2500 v/v/hr.

14. The process of claim 1 wherein said catalyst is in the form of a fixed bed.

15. The process of claim 1 wherein said catalyst is in the form of a fluid bed.

16. The process of claim 1 wherein said catalyst is pretreated in step (a) for 16 hr. at 270° C. in 1:1 $H_2/CO$ at 1 atm. total pressure was 500 v/v/hr.

17. A process for producing $C_6$–$C_{12}$ liquid hydrocarbons, containing $C_6$–$C_{12}$ alcohols, comprising the steps of:
   (a) first contacting a supported catalyst composition comprising a mixture of iron oxide and thallium nitrate or oxide, the weight ratio of iron to thallium being about 100:10, taken as the free metals, by contacting said catalyst composition at about 270° C., with a 1:1 $H_2/CO$ volume ratio mixture at 0.1 MPa pressure and a space velocity of about 500 v/v/hr., to result in a partial, but not complete, reduction of said iron compounds to a mixture of trivalent and/or divalent iron and reduced and/or carbided iron; and
   (b) continuing said contacting as described in step (a) at a temperature of about 175° to 200° C., a space velocity of about 150 to 1200 v/v/hr., and a pressure of about 0.5 to 2.0 MPa to produce $C_6$–$C_{12}$ liquid hydrocarbons containing about 10 weight percent and higher $C_6$–$C_{12}$ alcohols.

* * * * *